United States Patent [19]

Laughlin et al.

[11] 4,031,202

[45] June 21, 1977

[54] CONTROLLED RELEASE CONTRACEPTIVE ARTICLE

[75] Inventors: Robert Gene Laughlin; Thomas William Gougeon, both of Cincinnati, Ohio

[73] Assignee: The Procter & Gamble Company, Cincinnati, Ohio

[22] Filed: Dec. 8, 1975

[21] Appl. No.: 638,775

[52] U.S. Cl. .................................. 424/28; 128/130; 128/260; 424/14; 424/16
[51] Int. Cl.² ........................................ A61M 31/00
[58] Field of Search ............................. 424/14–22, 424/28; 128/260, 263, 270, 271

[56] References Cited

UNITED STATES PATENTS

| | | | |
|---|---|---|---|
| 2,777,796 | 1/1957 | Elias | 424/28 |
| 3,108,043 | 10/1963 | Millman et al. | 128/270 |
| 3,760,805 | 9/1973 | Higuchi | 128/260 |
| 3,760,984 | 9/1973 | Theeuwes | 128/260 X |
| 3,845,770 | 11/1974 | Theeuwes et al. | 128/260 |
| 3,948,254 | 4/1976 | Zaffaroni | 128/260 X |

*Primary Examiner*—Dolph H. Torrence
*Attorney, Agent, or Firm*—Jerry J. Yetter; Julius P. Filcik; Richard C. Witte

[57] ABSTRACT

Controlled release articles which regulate the concentration of a surfactant compound at a useful level in an environment external to said articles are provided with a coating. The improved articles are especially useful in or on the bodies of animals, including humans, to provide immediate release of the coating and, thereafter, to provide controlled release of surfactants having biological activity, e.g., non-hormonal contraceptives.

11 Claims, No Drawings

CONTROLLED RELEASE CONTRACEPTIVE ARTICLE

BACKGROUND OF THE INVENTION

The present invention encompasses articles designed to provide substantially immediate release of a desirable material present on the outside of the articles, and during a subsequent time period to provide controlled release of surfactant compounds contained within the articles. More specifically, the articles herein are characterized by a container having any desired material (e.g., a biologically active agent) releasably affixed on the outer surface, said container releasably enclosing a solution of a micelle-forming surfactant compound which can migrate from the container via a microporous membrane.

The desirability of providing metered dosage forms of biologically active or medicinal agents has long been recognized. Metered dosages can be manifest either as "controlled release" or "sustained release" of a given material. The distinction between controlled release and sustained or prolonged release has been recognized; see Cowsar, in "Advances in Experimental Medicine and Biology", Vol 49, "Controlled Release of Biologically Active Agents", Ed. Tanquary and Lacey, Plenum Press, New York 1974.

The copending application of R. G. Laughlin, entitled CONTROLLED RELEASE ARTICLES, filed Mar. 19, 1975, Ser. No. 560,020, now abandoned, the disclosures of which are incorporated herein by reference, succinctly describes controlled release and sustained release articles. The application also discloses controlled release articles comprising a micelle-forming surfactant and a microporous membrane of the type employed in the improved articles herein.

Briefly stated, controlled release articles respond rapidly to changes such as dilution effects in the environment external to the article, e.g., by body fluid changes, whereas sustained release articles do not. The net result is that articles based on the principle of controlled release are capable of rapidly establishing an effective level or concentration of a medicament or other agent in a selected environment, and then shutting off release so as to maintain the concentration at that level. In contrast, sustained release articles simply dispense an agent at a constant rate and do not display the feedback regulation of release that a controlled release article displays.

It will be appreciated that articles operating by the controlled release mechanism provide substantial advantages over sustaining release articles for certain uses. For example, placement of a properly formulated controlled release medicament system in an animal's body cavity in contact with body fluids establishes and maintains an effective concentration of the medicament in the fluids. The system responds to dilution or depletion as additional fluids are secreted, or the medicament is bound to tissue, absorbed, etc., thereby automatically maintaining the concentration of medicament at the proper level.

A controlled release article requires an initial period of time to establish an effective concentration of the agent being released in the environment external to the article. This time lapse may be unacceptable; for example, in vaginal contraceptives it may be important to provide an effective amount of a contraceptive agent immediately. The present invention provides a solution to this problem.

As disclosed in the application of Laughlin, above, solutions of micelle-forming surfactant compounds can be releasably enclosed in a container comprising a microporous membrane. Articles prepared in this manner are stable and do not suffer osmotic rupture when placed in body cavities in contact with body fluids. Rather, the stable articles provide controlled release of the surfactant into the body fluids. The proper selection of surfactant provides a means for achieving various biological effects, e.g., antimicrobial activity, spermicidal activity, and the like. Such articles can be used in any situation where controlled release of a surfactant into an external fluid medium is desired and, while especially useful in body cavities such as the vagina, are not limited to such use.

By the present invention the foregoing type of article is provided with an outer layer or coating of and agent (which need not be a surfactant) which is immediately released on contact with the environment in which the article is placed, e.g., a body cavity. A quantity of this outer agent sufficient tc provide the desired response is therby provided immediately. Controlled release and maintenance of an effective amount of the surfactant then ensues.

The following United States patents relate to articles comprising drugs enclosed with permeable membranes: U.S. Pat. No. 3,828,777 MICROPOROUS OCULAR DEVICE, issued Aug. 13, 1974 to R. A. Ness; U.S. Pat. No. 3,618,604 OCULAR INSERT, issued Nov. 9, 1971 to R. A. Ness; U.S. Pat. No. 3,416,530 EYEBALL MEDICATION DISPENSING TABLET, issued Dec. 17, 1968 to R. A. Ness; U.S. Pat. No. 3,832,252 METHOD OF MAKING A DRUG-DELIVERY DEVICE, issued Aug. 27, 1974 to T. Higuchi and H. M. Leeper. (See also U.S. Pat. No. 3,598,122, issued 10/1971, other references cited in Higuchi, et al., as well as U.S. Pat. No. 3,867,519.)

In general, the foregoing references relate to sustained release articles, rather than controlled release articles. The Higuchi, et al., patent illustrates the use of internal barriers in an article to achieve sustained drug release in the manner noted hereinabove. None of the references suggest the present articles which provide both immediate and controlled release of desirable agents.

Attwood and Florence, J. Pharm. Pharmac., 1971, 23, Suppl. 242S, briefly describe the dialysis of chlorpromazine across Visking membranes and suggest that this phenomenon may have applications in sustained release technology.. Attwood, et al., do not suggest articles of the present type.

Lichtman, et al., *Contraception* 8 (4) 291–7 (1973) describe a vaginal contraceptive device comprising a soluble film containing a nonionic surfactant as a spermicide.

U.S. Pat. No. 3,694,364 LAUNDERING AID, issued Sept. 26, 1972 to J. B. Edwards, relates to surface-modified cellulose bags (e.g., terry cloth) containing detergents and their use in laundry baths.

SUMMARY OF THE INVENTION

The present invention combines the desirable metered dosage features of controlled release articles with immediate delivery of an effective amount of any desired agent, e.g., a medicament, spermicide, or the like.

Briefly stated, the present articles comprise what can be characterized as an "immediate release active agent" releasably affixed to the outer surface of a container, said container enclosing a "controlled release active agent." For the reasons set forth herein, the selection of controlled release agent is limited to certain types of surfactants. However, the immediate release agents can be chosen from a much broader spectrum of materials.

DETAILED DESCRIPTION OF THE INVENTION

The articles herein comprise a controlled release agent which is a solution consisting essentially of a desirable micelle-forming surfactant compound and solvent, normally water, said solution having a concentration above the critical micelle concentration of the surfactant compound. The solution of the surfactant compound is releasably enclosed in an insoluble container (i.e., a container which maintains its physical integrity when in contact with fluids, especially water or biological fluids such as serum) at least part of the wall of said container comprising a microporous membrane. An effective amount (e.g., a unit dose) of an immediate release agent is releasably affixed to the outer surface of the container. This immediate release agent can comprise a unit dose of the surfactant contained within the articles, or can be another kind or type of agent, depending on the end use of the article.

The immediate release feature of the present articles is simply a manifestation of the removal of the external agent by dissolution, frictional effects, etc. The controlled release feature of the articles is a result of controlled diffusion of surfactant monomer through the solvent medium (typically water or biological fluids such as serum) in the pores of the microporous membrane portion of the enclosing container. The micellar solution of surfactant remaining in the container serves as a reservoir which automatically releases additional surfactant monomer through the membrane when the external monomer concentration is decreased.

Surfactants employed in the preferred articles designed for use in the body cavities of animals are characterized by an "R" value (as defined more fully hereinafter) greater than about 1.

The agents releasably affixed to the outer surface of the articles can be selected from a wide variety of materials, also more fully described hereinafter.

Preferred articles of the present type are especially useful as contraceptives which provide both immediate protection and which can remain in the vagina between menstrual periods to provide a constant level of contraceptive protection. Such articles comprise a container made wholly or partly of a microporous polymeric diffusion membrane (preferably cellulose), wherein said container encloses solution of spermicidal surfactant at a concentration greater than the critical micelle concentration (cmc) of the surfactant, and wherein said container has a effective amount of a spermicide releasably affixed to its outer surface. (The terms "spermicide" and "spermicidal" as employed herein are intended to encompass agents which truly "kill" animal sperm as well as those which immobilize or otherwise render sperm cells inactive.)

The use of micelle-forming surfactant solutions to provide the controlled release feature of the present articles results in several important advantages over other types of metered dosage systems. These advantages are perhaps best appreciated when considering the use of the articles as contraceptives.

The use of micelle-forming surfactants as the controlled release active agent in the articles maintains the osmotic pressure therein at a relatively low level. Accordingly, the pressure differential across the enclosing container is relatively small, and the container is stable and does not rupture. This desirable attribute of the present articles is to be contrasted with the situation which occurs when a similarly concentrated solution of a non-micelle-forming solute of similar molecular weight is enclosed in a diffusion membrane, whereupon osmotic pressures of tens or hundreds of atmospheres can be developed, thereby leading to rupture of the membrane.

Moreover, the surfactants employed as the controlled release active agent of the contraceptive articles of the present invention appear to function by an entirely localized effect on motile sperm. Accordingly, undesirable side-effects which can accompany the prolonged use of systemic contraceptive drugs such as hormones are avoided.

In addition, the use of safe, effective surfactants as the controlled release spermicide permits the formulator of the articles to employ a large excess of the spermicide therein. The controlled release feature allows formulation of articles containing more spermicide than the usual expected need but (1) reduces the probability of side-effects by regulating the concentration to a maximum level, and (2) allows for unusual variations in the amount of compound required or in the time period over which it might be needed. Accordingly, a "safety factor" of the order of 1,000-fold vis-a-vis prolonged contraceptive efficacy can be provided by the articles.

Finally, the contraceptive articles herein are designed for use in the vagina. Accordingly, the articles can be inserted by the user and do not require fitting by a physician as, for example, in the case of a diaphragm, or insertion by a physician as, for example, in the case of intrauterine devices. The articles provide both immediate and long-term contraceptive protection and can be retained in the vagina during the time between menstrual periods to provide the desired prolonged contraceptive protection.

The present articles are comprised of multiple components, each of which is described in detail hereinafter.

The article of manufacture encompassed by this invention comprises:

a. a stable, insoluble container, at least part of the wall of said container comprising a microporous membrane;
b. an agent releasably affixed to the outer surface of the article; and
c. a solution consisting essentially of:
   i. a micelle-forming surfactant compound, and
   ii. a solvent for said surfactant compound,
said solution having a concentration above the critical micelle concentration of the surfactant compound, said solution being releasably enclosed within the aforesaid container.

Preferred articles herein are those wherein the microporous membrane is cellulose, most preferably wherein the cellulose membrane comprises substantially the whole of the container and substantially envelops the solution of micelle-forming surfactant compound.

Immediate Release Agent

The agent which is releasably affixed to the outer surface of the articles herein (i.e., the immediate release agent) can be selected from a variety of materials, depending on the desired response and the intended use. Typically, the agent will be a biologically active material, a lubricant, or the like. The agent can be in the form of crystals, creams, salves, ointments, jellies, and the like.

For example, the immediate release agent can be a spermicide, especially non-hormonal spermicides such as the alkylene oxide nonionic surfactants. Such materials include the well-known condensation products of polyethylene oxide with an alcohol or alkyl phenol. Specific examples of such non-hormonal spermicides include nonylphenol pentaethoxylate, nonylphenol octaethoxylate, nonylphenol nonaethoxylate, n-dodecanol octaethoxylate, as well as the alkylene oxide nonionic surfactants described hereinafter for use within the articles of this invention.

The immediate release agent can also be selected from bacteria-controlling agents. Non-limiting examples of such agents include the various antibiotics such as the penicillins, the cephalosporins, the tetracyclines, the aureomycins, the streptomycins and the pharmaceutically acceptable salts thereof. Other bacteria-controlling agents include the polymyxins, the chloramphenicols, and the sulfonamides.

Other types of immediate release agents which can be releasably affixed to the outer surfaces of the articles herein include fungi-controlling agents. Specific examples of such agents include the griseofulvins and the odd-chain fatty acids, or the pharmaceutically acceptable salts thereof, e.g., zinc undecylenate.

Other types of actives which can be releasably affixed to the outer surfaces of the articles herein to provide immediate release and efficacy include anti-inflammatories such as hydrocortisone, cortisone, fluocinolone, triamcinolone, prednisolone, and the salts thereof.

Estrogens such as diethyl stilbestrol and the prostaglandins such as $PGE_1$, $PGE_2$ and $PGF_2\alpha$, can be employed as the immediate release agents herein.

Pharmacologically safe acids which temporarily lower the pH of vaginal fluids and/or cervical mucus can also be used as the immediate release agent. It is well known that maintaining the pH of the vagina and/or cervical mucus in the acid range is an effective contraceptive means. Such acids include, for example, tartaric acid, citric acid, boric acid, and the like.

Various microbiocides such as phenylmercuric chloride, benzethonium chloride, methyl benzethonium chloride, oxyquinoline sulfate, sodium N,N-dichlorosulfonamidobenzoate, and the like, can also be used as the immediate release agent.

Lubricating coatings such as cocoa butter, petrolatum, and the like, can be releasably affixed to the outer surfaces of the articles to provide ease-of-insertion.

It will be appreciated that, inasmuch as the immediate release agent is affixed to the outer surfaces of the articles herein to provide an immediate, desirable response, it is most preferable that an effective amount of the agent be thus affixed. Of course, the absolute amount used will depend on the type of agent, the desired response, the nature of the treatment, and the like. In any event, it is most desirable that a unit dose of the selected agent sufficient to provide the desired response be releasably affixed to the outer surface of the article. The unit dose will vary from a few milligrams or tenths of milligrams for hormones and antibiotics, to a few grams, for lubricant coatings. Mixtures of the various immediate release agents which amount to a unit does can also be used.

The immediate release agent can be deposited or coated on the containers. Alternatively, a plurality of containers can be joined by connecting means such as a strip of biologically inert plastic. In such instances, the connecting means can be used to carry the immediate release agent to the vaginal cavity.

Controlled Release Agent

The surfactants employed as the controlled release agent in the instant articles and processes are characterized by several parameters which can vary somewhat, depending on the ultimate use of the articles. In general, the surfactants are selected from those which, in combination with a microporous membrane (as described more fully hereinafter), provide an appropriate relationship between release and the desired end use of the article, e.g., spermicidal activity.

The surfactants herein are characterized by their ability to dissolve in a solvent (normally water) and to form an association colloid therein. The grossly anomalous (low) osmotic pressures displayed by concentrated solutions of the surfactants herein are attributable to the association of surfactant monomers into micellar structures. This phenomenon is of considerable practical significance in that it allows fabrication of articles containing surfactants at extraordinarily high concentrations, as compared with concentrations permitted with other, non-associative types of solutes, without osmotic rupture of the enclosing membrane. In order to realize fully the unique advantages of surfactants in this regard, it is preferred to use those surfactants having a cmc of at most about $1 \times 10^{-3}$ molar (M).

When intended for use as between-period contraceptives or to provide other desirable effects such as the controlled release of antimicrobial surfactants, it is, of course, necessary to select surfactants which produce the desired biological response. Moreover, to secure the benefits of controlled release it is necessary also to select surfactants whose monomers are rapidly transported through the diffusion membrane to establish and maintain an effective concentration of surfactant in the medium external to the article.

From the foregoing considerations it will be appreciated that the desired biological response of a surfactant can be tested in vitro in a medium (such as physiological saline, which closely approximates various body fluids) to determine the concentration at which the surfactant must be present in such medium to provide the desired response. Surfactants whose monomers are transported through the enclosing membrane of the article to provide at least the aforesaid effective concentration in the saline are useful herein. Over a given time period, the controlled release articles herein produce a stable maximum (or "plateau") concentration of surfactant in the external fluids. The magnitude of this plateau concentration is related to the cmc of the surfactant compound, and is approximately equal to the cmc. It follows that, for the desired effect to be realized, the ratio, R, of the cmc of the surfactant to its biologically effective concentration, $C_{biol.}$, in saline, i.e., $$R = cmc\ C_{biol.}$$

must be greater than about 1. Similar considerations hold for external media other than saline, i.e., fluid media such as body fluids, water, etc., in which the present surfactant monomers are soluble. Accordingly, the preferred compounds for use in the articles described herein have values of R which are greater than about 1, i.e., $$R > ca.\ 1$$

It will be recognized that a variety of surfactants exhibit a cmc less than the requisite about $10^{-3}M$ and meet this criteria for use in the present controlled release articles. Several surfactant types having the requisite cmc provide desirable biological responses, e.g., microbiocidal or static activity and/or spermicidal activity. Moreover, several surfactants exhibit thie requisite relationship, $R > ca.\ 1$, between cmc and biological activity.

Based solely on the foregoing considerations, representative examples of surfactants useful herein include nonionic surfactants such as $C_{10}H_{21}(OCH_2CH_2)_5OH$ (abb. $C_{10}EO_5$) and $C_{10}H_{21}(OCH_2CH_2)_6OH$ ($C_{10}EO_6$); semipolar surfactants such as $C_{12}H_{25}S(NH)_2CH_3$ and $C_{12}H_{25}(CH_3)_2AsO$; and cationic surfactants such as $C_{16}H_{33}N^+(CH_3)_3$, $Cl^-$ and $C_{16}H_{33}N^+C_5H_5,Cl^-$. These surfactants are characterized by $R \gtrsim 2$ and $cmc < 10^{-3}M$.

It is to be understood that other surfactants having the requisite cmc of $10^{-3}M$, or less, but which exhibit lower biological activity (especially as spermicidal agents), i.e., surfactants wherein ca. $1 < R < 2$, can be employed in the instant articles. However, the biological response to these latter surfactants is somewhat less than that of the preferred group, and the efficacy margin, i.e., R−1, is not as great. Included among this group of surfactants are $C_{12}EO_9$; $C_{16}EO_1SO_4^-$, $Na^+$; $C_{12}(CH_3)_2PO$; $C_{10}EO_4$; $C_{12}(C_2H_5)_2PO$; $C_{16}$ ammoniopropanesulfonate; $\beta$-$OHC_{12}(CH_3)_2PO$; and nonylphenol nonaethoxylate.

As can be seen from the foregoing, various surfactant types are useful for providing the controlled release feature of the present articles. However, when articles designed for use as between-period contraceptives are being prepared, additional physio-chemical properties of the surfactants must be considered. For example, the surfactants should be toxicologically acceptable for use in the body over extended time periods. The surfactants should also be non-irritating to the delicate tissues of the vagina and uterus. The surfactants should not substantially bind soluble proteins found in the vaginal fluids between periods of menstrual flow, inasmuch as the bound surfactant-protein moiety does not function as a spermicide and undesirably accelerates the depletion of surfactant from the reservoir within the article. Finally, the surfactant should be selected from those which do not bind to ionically charged sites in the enclosing diffusion membrance, since binding leads to unregulated transport through the membrane.

Based on the foregoing factors, and considering the high spermicidal activity of the compounds, the $C_{10}EO_5$ and $C_{10}EO_6$ surfactants are most preferred for use in he present contraceptive articles. As between these latter compounds, $C_{10}EO_5$ has the advantage of the lower molecular weight, and therefore provides more monomer per given weight of compound. Accordingly, $C_{10}EO_5$ is most preferred for use in the between-period, controlled release contraceptive articles of this invention.

Importantly, the nonionic surfactants do not undesirably interact with the agents which are releasably affixed to the outside of the articles herein.

It will be recognized that the surfactants disclosed hereinabove are all well known from the detergency arts and can be made by various art-disclosed processes.

It is to be understood that mixtures of surfactants result in the formation of mixed micelles and preferential migration of the more soluble monomer. Monomer release from mixed surfactants is, therefore, not rigorously controlled. Such surfactant mixtures are operable herein, but pure surfactants are more preferred.

Container

Broadly, the present articles comprise the external agent, the container, and the enclosed surfactant solution. At least one portion of the container comprises a microporous membrane which permits the controlled release of surfactant monomers into the environment external to the container, but which prevents the transport of the larger surfactant micelles. In short, the membrane acts as a selective "sieve" at the colloidal/molecular level.

Containers used in the present articles can be partly made of any stable material such as glass, plastic, etc., which is not permeable, even to surfactant monomers. Of course, the container should be made from a material which is inert to both the externally applied immediate release agent and to the surfactant solution, but selection of inert container materials is not a problem.

At least some portion of the container used herein must comprise the microporous membrane to allow controlled monomer release. Preferred articles are those wherein the container comprises an envelope of the membrane.

The membranes used in the articles are characterized by parameters which reflect their strength, integrity and ability to act as a selective sieve for surfactant monomers, as follows.

The membranes should be substantially water-insoluble so that they maintain their strength and integrity when in contact with body fluids. (Of course, if the articles are to be used in contact with other types of fluids, appropriate solubility relationships must be considered.)

The membranes should be of a thickness (wet) less than about 150 microns ($\mu$) and are most perferably about 25–50$\mu$ thick (wet). Membranes thicker than about 150$\mu$ (wet) tend to impede release of surfactant monomer, whereas thicknesses below ca. 5–10$\mu$ (wet) cause the articles to be subject to osmotic rupture even by the relatively low osmotic pressure of the concentrated surfactant solutions used in the articles.

When the articles are to be used in contact with body fluids and tissues, as in the contraceptive articles herein, the membranes (and total container) should be toxicologically acceptable. Moreover, the membrane material will most preferably be immunologically acceptable and will not be rejected by the body's natural defense mechanisms nor have any untoward effect on the rate of antibody formation, and the like.

Finally, the membrane must have the ability to act as a sieve for the surfactant monomers in order to provide the controlled release benefit of the article. An important consideration in this regard is that the surfactant must not be soluble to any substantial extent in the membrane material. If the surfactant were to be soluble in the membrane material, uncontrolled release would ensue.

The membranes employed herein comprise a solid wall material having multiple miniscule pores therethrough, i.e., are microporous. The pores of the membrane are filled, or substantially filled, with solvent (e.g., water) for the surfactant monomer. In use in the containers of the instant articles, surfactant monomers migrate from the inner reservoir of micellar surfactant solution to the external environment by means of diffusion through the solvent in these solvent-filled pores, which pores extend from inner to outer surfaces of the articles.

It will be appreciated by those skilled in the art that pore diameters of the membranes herein cannot be specified in absolute terms. Indeed, when dealing with pore sizes at the molecular level (i.e., at the dimensions of surfactant monomers) measurement techniques are only indirect and generally constitute a determination of which molecules (or association colloids) will pass through a given membrane and which will be retained, coupled with approximations of the molecular dimensions of the molecules that do pass.

Based on the foregoing, the pores in the membranes used in the present articles are characterized by diameters on the order of the size of the surfactant monomers herein, but are smaller than the surfactant micelles (i.e., association colloids comprising ca. 100–1000 monomer units). An experimental Surfactant Transport Procedure for selecting microporous membranes having the appropriate pore size for use in the articles is set forth below.

Membranes suitable for use as the container can be made from any material which possesses the above-described characteristics and properties. For example, suitably perforated polyethylene, polypropylene, polyvinylchloride, etc., sheeting can be used in the present articles.

Preferred membranes herein are prepared from water-swellable polymers such as polyvinyl alcohol (suitably modified so as to be water-insoluble) and cellulose. Cellulose is a highly preferred membrane material, inasmuch as it has a long history of safety when used in prolonged contact with animal tissue. Such swellable polymers (or polymer precursors) can be cast into membranes which swell to about 1.8 to 2.0 times their dry thickness on contact with water. This swelling action automatically opens pores in the polymer membrane, and these pores are of the proper size to permit passage of surfactant monomers, and to prevent passage of surfactant micelles, through the membrane.

Methods for casting swellable cellulose membranes are well known and form no part of this invention. In general terms, a cellulose derivative (e.g., cellulose acetate) is dissolved in a suitable solvent (e.g., acetone) and the solution is spread onto a smooth surface, whereupon the solvent evaporates leaving a continuous film of the cellulose derivative. The film of cellulose derivative is thereafter converted back to cellulose using an aqueous ammonia solution and swollen with water to provide a membrane suitable for use as the container of the present articles.

As will be appreciated from the foregoing, a variety of materials can be used as the membranous container portion of the controlled release articles, with solvent-swellable polymers being the most preferred due to their inherent sub-microscopic porosity in the swollen state. An experimental procedure which can be used to select membranes for use herein is as follows.

Surfactant Transport Procedure

A cell for testing transport of surfactant monomers through membranes, thereby providing a means for selecting membranes for use herein, is as follows. A 40 mm (diameter) × 50 mm (length) polymethylmethacrylate rod is halved and each half is suitably machined to provide cavities 16 mm (diam.) × 10 mm (depth), such that the cavities abut when the rod halves are reassembled. Each cavity is provided with two inlets holes for filling and sampling. A brass clamp is used to hold the two cell halves firmly together.

The surfactant transport testing is carried out in the following manner. A 4 cm. × 4 cm. square of the membrane material to be tested is sandwiched between the cell halves, enclosing a 3 mm. glass bead on each side of the membrane to provide stirring. The cell cavities are filled with saline and the inlet holes are plugged with waterproof tape. After equilibrating overnight at 37° C, the saline in one half of the cell is replaced with a solution of known concentration of radiotagged surfactant. The inlet hole is again taped, and the cell is placed in a 37° bath in a device which allows the cell to be rotated axially at 50 rpm. Periodically, the cell is raised from the bath and the solution in the desired compartment sampled.

A typical procedure using a membrane cut from viscose cellulose dialysis tubing (Matheson Scientific, 18970-14 20) is as follows. After equilibrating the cell and charging one side with surfactant as above, the cell is maintained in the 37° C bath for varying time periods, after each of which the tape is removed from the inlet holes and 10 microliter ($\mu$l) samples are removed by syringe. The samples are expressed below the surface of 100 $\mu$l of distilled water in a counting vial. In the subsequent scintillation counting, each sample vial is charged with 10 $\mu$l of a solution of 0.8% 2-diphenyloxazole and 0.01% of 1,4-bis-[2-(4-methyl-5-phenyloxazolyl)]-benzene in a 1:1 ethanol/toluene mixture. The vials (one for each time period) are then placed in the refrigerator compartment of a counting instrument and cooled to 4° C before being counted for 5 minutes each. The counts per minute are converted to ppm by applying a factor found by counting one or more standard samples. By taking samples at regular intervals, a curve plotting the surfactant concentration in the initially surfactant-free side of the cell versus the time of sampling can be drawn which describes the transport of the surfactant across the membrane.

Following the Surfactant Transport Procedure set forth hereinabove, the cell cavity designated (A) is charged with surfactant solution and the cavity designated (B) is charged with saline. The cell, whose cavities are separated by the test membrane, e.g., swollen, microporous cellulose dialysis tubing (dry thickness 25$\mu$; swollen thickness 50$\mu$) is then equilibrated in the indicated manner. The concentration of surfactant transported to cavity (B) is determined in the foregoing manner, and the graph of the concentration of surfactant in (B) v. time is plotted.

A plot of the concentration (B) as the ordinate and time (t) as the abscissa describes a monomer transport curve which rises sharply at the outset, and which gradually flattens. The slope of the sharply rising portion of the curve (i.e., over the first five hours of surfactant monomer transport) is the primary slope, $S_1$, and that of the flattened portion of the curve (i.e., 20 hours, and longer, of monomer transport) is the secondary slope, $S_2$.

To achieve the controlled release feature of the articles of the present type, the combination of surfactant and membrane should yield a monomer transport curve wherein $S_1$, i.e., $d[B]/dt$ ; $t \times 0 - 5$ hrs.

is reasonably steep, and $S_2$, i.e., $d[B]/dt$ ; $t > 20$ hrs.

is reasonably flat, ideally zero. The intercept at zero time of the secondary transport data, having slope $S_2$, should be about equal to the cmc of the surfactant being tested. The ratio of $S_2/S_1$ is from 0 to about 0.1. $S_1$ should be no less than about $50 \times 10^{-6}$ moles $l^{-1}$ hr.$^{-1}$, and preferably should be in the range of about $200 \times 10^{-6}$ moles $l^{-1}$ hr.$^{-1}$ to about $750 \times 10^{-6}$ moles $l^{-1}$ hr.$^{-1}$.

Based on the foregoing, surfactant/membrane combinations can be selected which will provide the controlled release feature in articles of the present type. A highly preferred article which is particularly useful as a controlled release vaginal contraceptive comprises from about a 5% to about a 50% (wt.) aqueous solution of $C_{10}EO_5$ enclosed within a microporous, swollen cellulose membrane (dry thickness ca. $25\mu$; swollen thickness ca. $50\mu$).

The following non-limiting examples illustrate articles of the present type which are suitable for use as vaginal contraceptives, and the like.

EXAMPLE I

A flat sheet of commercial cellulose acetate about $75\mu$ thick and measuring about 7 in. $\times$ 10 in. is subjected to thermoforming methods known in the art to produce six hemispherical indentations 1 in. in diameter in the sheet. These indentations are filled to ca. 25% of their total volume with pure $C_{10}EO_5$ surfactant (using ca. 1 ml. of surfactant). A second flat sheet of cellulose acetate film is solvent-sealed over the original sheet covering the indentations using techniques known in the art.

The individual filled and sealed indentations are then cut from the composite sheet to provide six articles which are then immersed in a 7.4 M ammonia solution containing 10% by weight sodium chloride for 96 hours at 50° C. This ammonia treatment regenerates cellulose by deacetylating the cellulose acetate. Water passes through the membrane under the influence of osmotic forces during the deacetylation, partially filling the sealed articles.

Following the ammonia treatment, the articles are immersed in distilled water, whereupon they fill completely under the influence of osmosis, the entrapped air diffusing out leaving an article consisting of a closed container of regenerated cellulose enclosing a ca. 25% solution of $C_{10}EO_5$ surfactant. An article of this type exhibits a monomer transport curve with $S_2/S_1$ of ca. 0.

Following the above deacetylation procedure, the outer surfaces of the above articles are uniformly coated with ca. 0.7 g. of $C_{10}EO_5$ surfactant per article.

An article of the foregoing type is placed in the vagina posterior to the introitus. The outer coating of $C_{10}EO_5$ is released into the vagina to provide a contraceptive effect immediately. The article is worn during the time between menses and safely delivers a spermicidally effective amount of $C_{10}EO_5$ to the vaginal area throughout this time.

In the article of Example I the $C_{10}EO_5$ surfactant used both as the immediate release and as the controlled release agent is replaced by an equivalent amount of $C_{10}EO_6$ (again, as each agent) and the equivalent results are secured.

In the article of Example I the pure $C_{10}EO_5$ is replaced by an equivalent amount of a 90:10 (wt.) mixture of $C_{10}EO_5$ and $C_{10}EO_6$ and good spermicidal activity, both immediately and over about a 21-day period, is secured.

In the article of Example I the outer coating of $C_{10}EO_5$ is replaced by an outer coating of 0.7 g. of nonylphenol nonacethoxylate. On placement of the article in the vagina, the nonylphenol nonaethoxylate provides an immediate spermicidal effect, whereas the $C_{10}EO_5$ contained within the article is released in controlled fashion and provides a spermicidal effect over a 21-day time span.

EXAMPLE II

A lubricated article especially useful as a contraceptive device is as follows.

Polyethylene tubing ca. 2 mm. diameter $\times$ 2. cm. long is dipped in a solution of cellulose acetate/acetone and withdrawn, thereby depositing a film of cellulose acetate on the tubing. The acteone solvent is allowed to evaporate, thereby solidifying the cellulose acetate on the tubing. The cylindrical cellulose acetate film (thickness of about $25\mu$) is thereafter removed from the polyethylene form and one end is sealed by dipping in a droplet of cellulose acetate/acetone.

The foregoing cylinder, sealed at one end, is filled to about 75% of its volume with a 50% (wt.) aqueous solution of $C_{10}EO_5$ surfactant. The open end of the cellulose acetate cylinder is sealed in the above-described manner.

The cylinder containing the $C_{10}EO_5$ solution is deacetylated using 3.7 M aqueous ammonia containing 10% sodium chloride at room temperature for 48 hours. Thereafter, the filled cylinder is immersed in water for several hours, allowing substantially all of the residual ammonia and sodium chloride to diffuse into the water bath.

The filled cylinder prepared in the foregoing manner is coated with ca. 0.1 g of a gelled lubricant. The lubricant consists of 1.5% (wt.) of sodium carboxymethylcellulose (gelling agent); 0.1% (wt.) sodium p-aminobenzoate (antimicrobial); 50% (wt.) $C_{10}EO_6$ (spermicide); the balance comprising water.

An article prepared in the foregoing manner is inserted into the vagina posterior to the introitus. The $C_{10}EO_6$ is released immediately. The article is left in place over a period of 21 days and provides a spermicidally effective concentration of $C_{10}EO_5$ during that time.

What is claimed is:

1. An article of manufacture especially adapted for use as a contraceptive, comprising:

a. a stable, insoluble container, at least part of the wall of said container comprising a microporous cellulose membrane;
b. a spermicidal alkylene oxide nonionic surfactant releasably affixed to the outer surface of the article; and
c. a solution consisting essentially of:
  i. a micelle-forming spermicidal alkylene oxide nonionic surfactant compound, and
  ii. a solvent for said surfactant compound, comprising water,
  said solution having a concentration above the critical micelle concentration of the surfactant compound, said solution being enclosed within the container.

2. An article according to claim 1 wherein the membrane substantially envelops the solution of micelle-forming surfactant compound.

3. An article according to claim 1 wherein the nonionic surfactant releasably affixed to the outer surface of the article is the condensation product of polyethylene oxide with an alcohol or alkyl phenol.

4. An article according to claim 1 wherein the surfactant compound enclosed within the container is characterized by a critical micelle concentration of at most about $1 \times 10^{-3}$ Molar.

5. An article according to claim 4 wherein the combination of surfactant solution and membrane exhibits a monomer transport curve having a ratio of slopes $S_2/S_1$ in the range of 0 to about 0.1.

6. An article according to claim 5 wherein the surfactant has an R value greater than 1.

7. An article according to claim 1 wherein the nonionic surfactant enclosed within the container is selected from the ethylene oxide condensates of aliphatic alcohols, or mixtures thereof.

8. An article according to claim 7 wherein the nonionic surfactant is $C_{10}EO_5$.

9. An article according to claim 7 wherein the nonionic surfactant is $C_{10}EO_6$.

10. An article according to claim 7 wherein the solution within the container consists essentially of a nonionic surfactant selected from $C_{10}EO_5$, or $C_{10}EO_6$, or mixtures thereof; wherein the solvent is water; wherein the container comprises a microporous, water-swollen cellulose membrane having a dry thickness of ca. 5–25$\mu$ and a swollen thickness of ca. 10–50$\mu$; and wherein said container substantially envelops said solution.

11. An article according to claim 10 wherein a unit dose of a water-soluble alkylene oxide nonionic spermicidal surfactant is releasably affixed to the outer surface of the article.

* * * * *